United States Patent

Tramposch et al.

Patent Number: 4,861,798
Date of Patent: * Aug. 29, 1989

[54] LIPOXYGENASE INHIBITORY COMPOUNDS

[75] Inventors: Kenneth M. Tramposch, Williamsville; Fred C. Zusi; Suresh A. Marathe, both of Tonawanda, all of N.Y.

[73] Assignee: Bristol-Myers Company, New York, N.Y.

[*] Notice: The portion of the term of this patent subsequent to Mar. 15, 2005 has been disclaimed.

[21] Appl. No.: 133,601

[22] Filed: Dec. 22, 1987

Related U.S. Application Data

[63] Continuation-in-part of Ser. No. 947,334, Dec. 29, 1986, Pat. No. 4,731,382.

[51] Int. Cl.$^4$ ............... C07C 87/10; A61K 31/185
[52] U.S. Cl. ............... 514/575; 558/414; 560/144; 562/621; 562/426; 562/437; 562/443; 562/444; 562/449; 562/448
[58] Field of Search ............... 260/500.5 H; 514/575; 558/414; 560/144

[56] References Cited

U.S. PATENT DOCUMENTS

| | | | |
|---|---|---|---|
| 2,397,508 | 4/1946 | Rouault et al. | 260/550.5 H |
| 4,604,407 | 8/1986 | Haslanger et al. | 514/575 |
| 4,731,382 | 3/1988 | Zusi et al. | 514/575 |

FOREIGN PATENT DOCUMENTS 59-46244  3/1984  Japan .

Primary Examiner—J. E. Evans
Attorney, Agent, or Firm—David M. Morse

[57] ABSTRACT

Compounds of the formulae

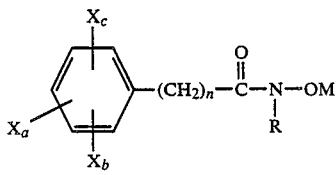

wherein $n=6-11$, M is hydrogen or a pharmaceutically acceptable cation, R is hydrogen or $C_1$–$C_6$ alkyl optionally substituted by a carboxyl group and $X_a$, $X_b$ and $X_c$ each independently represent hydrogen or a variety of substituent groups are potent inhibitors of 5-lipoxygenase.

19 Claims, No Drawings

LIPOXYGENASE INHIBITORY COMPOUNDS

CROSS-REFERENCE TO RELATED APPLICATION

This is a continuation-in-part application of co-pending application Ser. No. 947,334, filed Dec. 29, 1986.

BACKGROUND OF THE INVENTION

1. Field of the Invention

The present invention relates to novel hydroxamic acid compounds which inhibit the enzyme, 5-lipoxygenase. The metabolism of arachidonic acid via 5-lipoxygenase gives rise to products implicated as mediators in certain inflammatory and allergic disease states. Inhibition of 5-lipoxygenase blocks the production of such mediators and alleviates the inflammatory and allergic conditions resulting therefrom.

2. Description of the Prior Art

The literature reveals a large number of hydroxamic acid derivatives, some of which possess lipoxygenase-inhibitory activity and/or pharmaceutical activities associated with inhibition of lipoxygenase enzymes.

At the Gordon Conference in Medicinal Chemistry held July 28–Aug. 1, 1986 in New London, N.H. a handout was distributed disclosing, inter alia, compounds of the formula

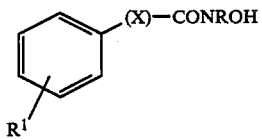

as 5-lipoxygenase inhibitors. Biological data was provided for phenylalkylhydroxamic acids of the formula

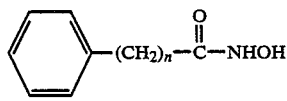

where n=0, 1, 2 or 3, but no mention was made of compounds with longer alkyl groups such as the n=6-11 compounds of the present invention. These compounds were also disclosed at the 1986 Fall American Chemical Society Meeting (Sept. 8, 1986–Sept. 12, 1986) in Anaheim, Calif.

Japanese Kokai 59/46244 in the name of Nissan Chemical Co. discloses hydroxamic acid derivatives of the formula

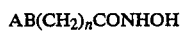

where A is $RX_m$ in which
  R is phenyl, pyrrolyl, thienyl, imidazolyl or thiazolyl;
  X is halogen, lower alkyl, lower alkoxy or nitro;
  m is 0, 1, or 2;
  the X substituents may be the same or different;
  B is —CHOH—, —CH$_2$—, —O— or —CO— and n=2-10 as antiprotozoal agents. The only compound disclosed where B is —CH$_2$— and A is phenyl is the compound of the formula

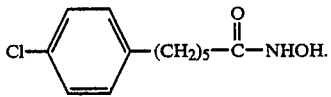

There is no mention of lipoxygenase-inhibitory activity. Applicants have tested the corresponding unsubstituted phenyl compound of the formula

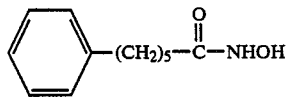

in the 5-lipoxygenase inhibition test reported in the text below and have found such compound to have an IC$_{50}$ ($\mu$M) of >100 compared with an IC$_{50}$ value of 20.9 for the compound of the present invention having the formula

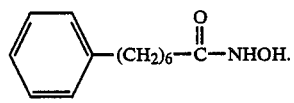

European patent application 161,939 discloses substituted benzohydroxamic acids of the formula

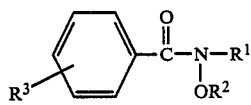

where, inter alia, R$^1$ and R$^2$ may be hydrogen, as lipoxygenase inhibitors. They may be distinguished from the present compounds by the lack of a carbon chain between the phenyl ring and the hydroxamic function.

K. Tanaka, et al. in *Chem. Pharm. Bull.* 31: 2810–2819, 1983, disclose some substituted phenylpropionohydroxamic acids of the type

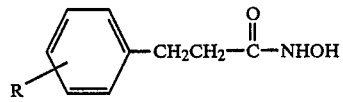

which are reported to have antiinflammatory activity. These compounds are distinguished from the present compounds by having a shorter alkyl chain length which has been found to be inappropriate for good activity.

U.S. Pat. No. 4,564,476 discloses a series of lipoxygenase inhibitors of the general formula

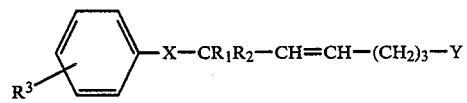

in which, inter alia, R$_1$, R$_2$ and R$_3$ may be hydrogen, X is O or CH=CH and Y may be —CONHOH. The compounds may be distinguished from the present compounds in that (1) they must have at least one double bond plus one heteroatom or at least two double bonds in the sidechain and (2) there is no specific diclosure of compounds having the hydroxamic acid group.

E. J. Corey et al. in *J. Amer. Chem. Soc.* 106: 1503-1504, 1984, discloses the compound

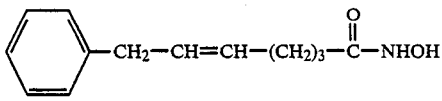

as a lipoxygenase inhibitor. This compound may be distinguished from the present compounds by the presence of the double bond in the sidechain.

U.S. Pat. No. 3,328,138 generically discloses hydroxamic acids of the formula

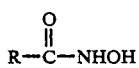

where, inter alia, R may be alkyl substituted by aryl, the entire radical having from 7-28 carbon atoms, as motor fuel additives.

U.S. Pat. No. 3,479,396 discloses compounds of the formula

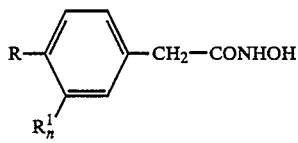

where R and $R^1$ can be alkyl, cycloalkyl, alkoxyloxy, alkenyloxy, cycloalkenyloxy, alkylthio, cycloalkyloxy, cycloalkylalkyloxy or arylalkyloxy; $R^1$ can also be hydrogen, and n is an integer of 0 to 2 as having antipyretic, antiinflammatory, antispasmodic and analgesic properties. These compounds have only one carbon atom in the alkyl chain.

U.S. Pat. No. 4,188,338 discloses, inter alia, ring-substituted compounds of the type

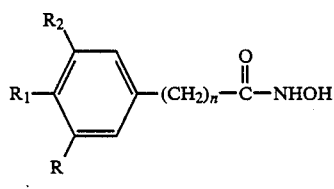

where R is alkoxy, alkenyloxy, alkyl or benzyloxy, $R_1$ and $R_2$ are H, alkoxy, alkenyloxy, benzyloxy or alkyl and n=2-3 as having inhibitory activity against blood platelet aggregation. In the specification (column 1, lines 20-60) it is stated that as the chain length increases the antiinflammatory activity *decreases* and that the disclosed compounds specifically have *no antiinflammatory activity* (column 2, lines 43-50). This leads away from expecting potent antiinflammatory activity in compounds where n is $\geq 2$ such as those of the present invention where n=6-11.

Japanese Patent 61/33,115 discloses a series of naphthyloxyalkyl hydroxamic acids of the formula

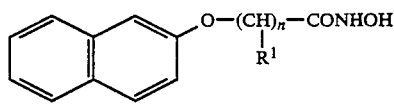

$R^1 =$ H when n = 1-10 as antiinflammatory agents. These compounds may be distinguished from the present compounds by the presence of the oxygen atom in the sidechain and a naphthyl instead of a phenyl group.

U.S. Pat. No. 4,579,866 (equivalent to Japanese 61/00054) discloses 5-lipoxygenase inhibitors of the formula

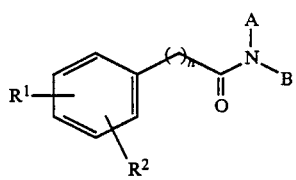

where $R^1$ and $R^2$ are independently H, OH, lower alkyl, lower alkoxy, aryloxy, heteroaryloxy, heteroaryl lower alkoxy, aryl, heteroaryl, aryl-lower alkyl, aryl-lower alkoxy, halogenated aryl-lower alkoxy, lower alkenyl, lower alkynyl, lower alkenyloxy, lower alkynyloxy, halogen or trifluoromethyl; A is H, aryl, lower alkyl, aryl-lower alkyl or heteroaryl; and B is

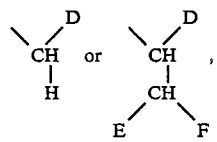

n=0-6,
wherein
D is H, $CONR_3R_4$, $CO_2H$, $CO_2R_5$, $CH_2OH$ or $CH_2OR_6$,
wherein
$R_3$, $R_4$, $R_5$ and $R_6$ are independently H, lower alkyl, aryl, aryl-lower alkyl or heteroaryl; E is H, OH, lower alkyl, aryl or heteroaryl; and F is

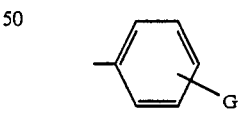

in which G is the same as $R_1$ and $R_2$. The present compounds may be distinguished by the presence of a hydroxamic functional group which has been found necessary for good activity.

U.S. Pat. No. 4,608,390 discloses compounds of the formula

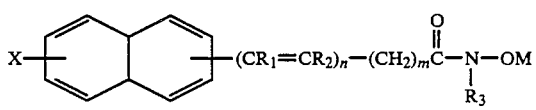

where

X is H, $C_1$–$C_{22}$ alkyl or alkenyl, or an electron-withdrawing group;

n is 0 or 1 and m is 0, 1, 2 or 3; but n and m are not 0 simultaneously;

$R_1$ and $R_2$ independently are H, $C_1$–$C_6$ alkyl, an electron-withdrawing group or $R_4$;

$R_3$ is H, $C_1$–$C_6$ alkyl or cycloalkyl, or $R_4$; and $R_4$ at each occurrence, has the formula

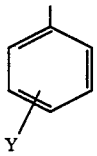

where Y is hydrogen or an electron-withdrawing group; and wherein M is a pharmaceutically acceptable cation, as lipoxygenase inhibitors. Among the compounds designated as Ex. Nos. 18 and 19 are those of the formula

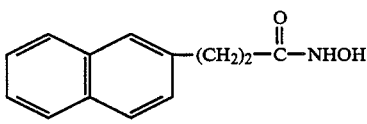

and

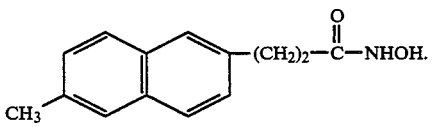

These compounds may be distinguished from the present compounds by the presence of a naphthyl instead of a phenyl group and a shorter alkyl chain.

U.S. Pat. No. 4,605,669 discloses lipoxygenase-inhibiting naphthohydroxamic acids of the formula

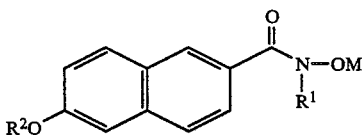

where $R^1$ is H or $C_1$–$C_6$ alkyl; $R^2$ is $C_1$–$C_{22}$ alkyl, cycloalkyl, aralkyl or alkenyl; and M is a pharmaceutically acceptable cation. These compounds have naphthyl instead of phenyl and have no alkyl chain.

European Patent Application 199,151 A2 discloses lipoxygenase-inhibiting compounds of the formula

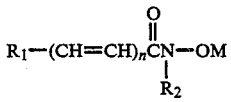

where $R_1$ is trinuclear aromatic or biaryl group; $R_2$ is hydrogen or $C_1$–$C_6$ alkyl or cycloalkyl; n is 0 or 1; and M is a pharmaceutically acceptable cation. Again, these compounds do not have a phenyl group in the sidechain and have either no alkyl chain or a double bond in the chain.

European patent application 196,674 discloses lipoxygenase-inhibiting hydroxamate compounds of the formula

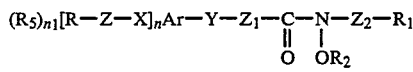

where $R_2$ is H, lower alkyl, formyl or $C_2$–$C_{10}$ alkanoyl; R and $R_1$ are each independently hydrogen, lower cycloalkyl, fused cycloalkyl or lower alkyl-substituted fused cycloalkyl, lower alkyl, phenyl, naphthyl or a nitrogen, oxygen or sulfur heterocyclic ring or heterocyclic-lower alkyl;

Z, $Z_1$ and $Z_2$ are each a chemical bond or an alkylene chain or a mono- or disubstituted alkylene chain containing up to 6 carbon atoms in the principal chain and up to a total of about 10 carbon atoms, a lower cycloalkyl, a nitrogen, oxygen or sulfur heterocyclic ring or heterocyclic lower alkyl, or a mono- or di-substituted lower cycloalkyl or heterocyclic lower alkyl;

X and Y are each independently O, S, $CR_3$, $R_4$ or a chemical bond;

$R_3$ and $R_4$ are each independently H or lower alkyl; each $R_5$ is H, aryl, lower alkaryl, formyl, nitro, cyano, amino, lower aminoalkyl, lower alkylamino, lower aralkylamino, halo, trihalo alkyl, carbamoyl or aroyl;

n is an integer from 0–2; and $n_1$ is an integer from 1–2. By judicious selection of the appropriate variables, one can obtain compounds of the formula

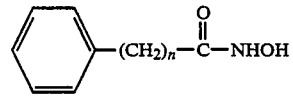

where n can be up to seven carbons in length. However, $Z_1$ is preferably only up to three carbon atoms in length, thus making the preferred compounds of the above formula those with $n \leq 4$. The lack of any specific disclosure of longer chain compounds together with the disclosed preference for $n \leq 4$ teaches away from applicants' compounds having n=6–11.

Despite the disclosure in the literature of various 5-lipoxygenase-inhibiting compounds as illustrated above, there is a need for more potent inhibitors of this enzyme.

SUMMARY OF THE INVENTION

Phenylalkyl hydroxamic acid compounds of the formula

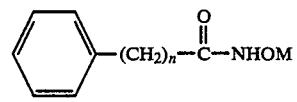

I wherein n is an integer from 6 to 11 and M is hydrogen or a pharmaceutically acceptable cation are novel and potent inhibitors of 5-lipoxygenase and are thus useful in the treatment of certain inflammatory and allergic disorders in mammals, e.g. humans, such as asthma and other chronic obstructive pulmonary diseases, arthritis, psoriasis, atopic eczema and chronic colitis.

DETAILED DISCLOSURE

The novel lipoxygenase-inhibiting compounds of the present invention are of the formula

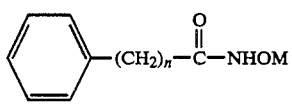
I wherein n is an integer from 6 to 11, more preferably 7-9 and most preferably 8, and M is hydrogen or a pharmaceutically acceptable cation.

The hydroxamic acid compounds of Formula I where M is hydrogen may be converted by methods known per se into pharmaceutically acceptable salts by reacting the acid with a suitable base providing a nontoxic cation. Suitable nontoxic cations may be based on the alkali metals and alkaline earth metals, e.g. sodium, potassium, lithium, calcium, magnesium, and the like. Also suitable are nontoxic ammonium, quaternary ammonium and amine cations such as ammonium, tetramethylammonium, tetraethylammonium, methylamino, dimethylamino, trimethylamino, triethylamino and ethylamino.

The compounds of Formula I may be prepared by known methods for the synthesis of hydroxamic acids.

One useful method is to start with commercially available phenylalkyl carboxylic acids of the formula

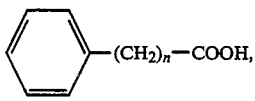

transform them to an activated acid derivative such as an ester, acid halide or anhydride and then condense the activated acid with hydroxylamine in the presence of base. This procedure may be illustrated by the following reaction scheme:

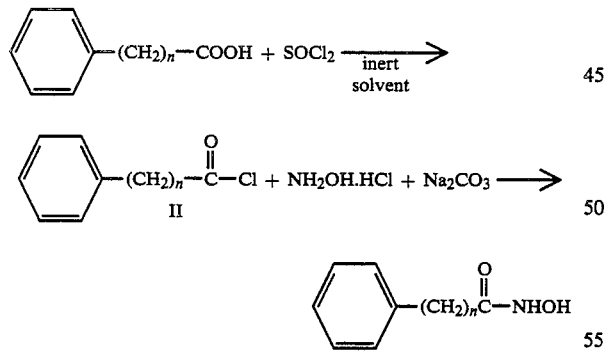

More particularly, the carboxylic acid is preferably converted to an acyl chloride by treatment with thionyl chloride in an inert solvent such as methylene chloride. The acid chloride is then condensed with hydroxylamine hydrochloride in the presence of a base such as $Na_2CO_3$ or triethylamine in an inert solvent such as methylene chloride.

In certain cases where the starting acids are not readily available, they may also be prepared by methods known in the art. For example, an $\alpha,\omega$-dicarboxylic acid may be condensed to a cyclic anhydride using a dehydrating agent such as acetic anhydride, and the cyclic anhydride may be condensed with benzene in the presence of a Friedel-Crafts catalyst such as aluminum trichloride to give an $\omega$-phenylketoacid. The ketoacid may then be reduced to the desired phenylalkyl carboxylic acid by reducing agents such as zinc amalgam. This process is illustrated in the following reaction scheme:

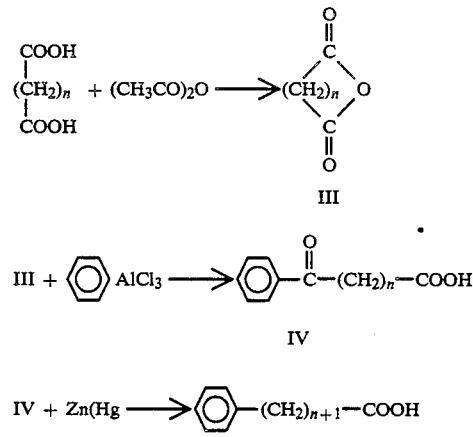

In still other cases, especially long-chain dicarboxylic acids where the cyclic anhydride III is not readily formed, the desired intermediate ketoacid IV can be obtained by protecting the diacid as the diester, deprotecting only one end of the diester by limited hydrolysis, converting the deprotected acid to an acyl halide, condensing the acyl halide with benzene to give a protected phenylketoester, and hydrolyzing the ester by known methods. This procedure is illustrated by the following scheme:

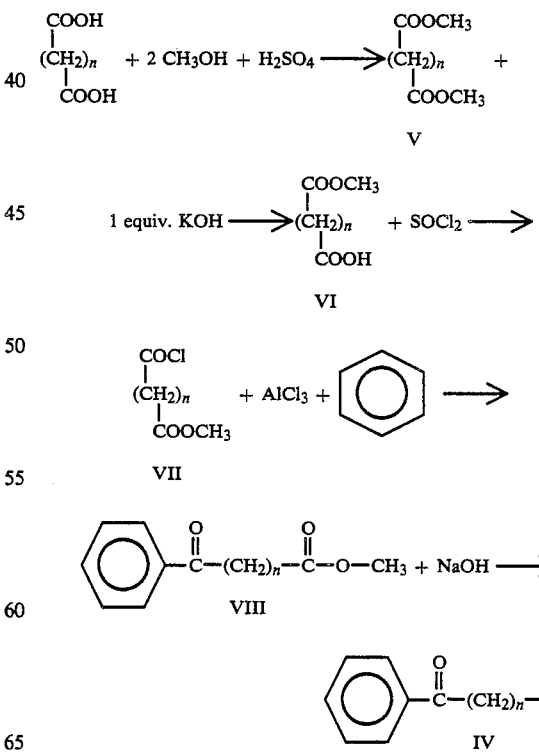

These ketoesters IV may then be carried forward as described above.

Compounds of Formula I have been found to have potent inhibitory activity against 5-lipoxygenase enzyme when tested in a mixed neutrophil/platelet system. This test is a measure of the inhibition of the synthesis of lipoxygenase products generated by human neutrophils and platelets. The protocol is similar to that described in the article "Comparative Effects of Indomethacin, Acetylenic Acids, 15-HETE, NDGA and BW755C on the Metabolism of Arachidonic Acid in Human Leukocytes and Platelets", H. Solari, P. Braquet and P. Borgeat, *Prost. Leuk. Med.* 13, pp. 53–60, 1984.

Human neutrophils and platelets were obtained from the blood of normal volunteers. The blood was collected into tubes containing EDTA as an anticoagulant. The blood was centrifuged at 250×g for 15 minutes and the platelet rich plasma was removed. The cell fraction was mixed with an equal volume of 0.9% saline containing 10 mM dextrose and resuspended in Dulbecco's phosphate buffered saline (PBS) without $Mg^{++}$ and $Ca^{++}$ and was counted. The cell suspension was adjusted to give a leukocyte count of $2-3\times10^7$ cells/ml. The platelet contamination in these preparations was 0.1 to 0.5 platelets/leukocyte.

Test compounds were dissolved in ethanol and added to polypropylene tubes. To control tubes (drug-free) only ethanol was added. The ethanol was evaporated to dryness under a stream of argon and then 0.1 ml of the cell suspension ($2-3\times10^6$ cells) was added. This mixture was pre-incubated for 5 minutes at 37° and then the reaction was initiated by addition of $^3$H-arachidonic acid, calcium ionophore (A23187), and calcium ion. The final concentration of each component was: arachidonic acid, 10 uM; A23187, 1.25 mg/ml; calcium ion, 2 uM. After 5 minutes the incubations were stopped by addition of an equal volume of methanol. The tubes were spun at 11,000 g for 2 minutes to pellet the precipitated protein. The supernatant was analyzed by HPLC for 5-HETE. The formation of this product is indicative of 5-lipoxygenase activity. Test drugs were evaluated for their ability to inhibit 5-HETE formation. Percent inhibition of varying concentrations of test drugs was determined in duplicate by comparing the peak quantitation in the presence and absence (control) of drug. The results in Table I report the $IC_{50}$ values. The $IC_{50}$ values were calculated from log-dose response curves of pooled data from at least two experiments by linear regression analysis. Table I also includes, for comparison purposes, $IC_{50}$ data of compounds of the indicated formula having n values of <6 and >11.

TABLE I

Inhibition of Human Leukocyte 5-LPO

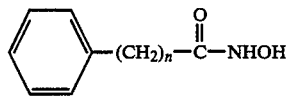

| Compound | n | $IC_{50}(\mu M)$ 5-LPO |
|---|---|---|
|  | 0 | >100 |
|  | 1 | >100 |
|  | 2 | >100 |
|  | 3 | >100 |
|  | 4 | >100 |
|  | 5 | >100 |
| 2a | 6 | 20.9 |
| 2b | 7 | 12.2 |
| 1 | 8 | 5.7 |
| 2c | 9 | 11.6 |
| 2d | 10 | 11 |
| 2e | 11 | 10.3 |
|  | 12 | >50 |
|  | 14 | >100 |

TABLE I-continued

Inhibition of Human Leukocyte 5-LPO

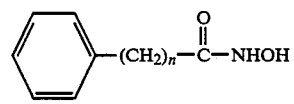

The compound of Formula I where n=8 was evaluated in the carrageenan sponge implantation model and found to have activity in this in vivo animal system predictive for inflammatory disease.

The carrageenan sponge implantation model is primarily used to measure the effect of antiinflammatory agents on cell infiltration. An acute inflammatory response is stimulated by the implantation of a small sponge beneath the skin of rats. The sponge normally contains an inflammatory stimulus such as carrageenan and produces a response which is characterized by infiltration of cells and accumulation of fluid. The number of cells in the exudate can be conveniently measured in the exudate fluid.

The compound of Example I was evaluated for its local effect on cell migration and mediator production in this model. For comparison, indomethacin and BW755C were also evaluated after local application. Polyester sponges were soaked in solutions of 0.5% carrageenan (in normal saline) which also contained 1% or 5% wt/vol of the test compound. The impregnated sponge was inserted through a small incision on the dorsal surface of a lightly anesthetized rat into a subcutaneous pocket formed by blunt dissection. The incision was then closed. The control treatment consisted of a sponge soaked in 0.5% carrageenan in normal saline. Animals were sacrificed 6 hours after sponge implantation. Sponges are dissected out an placed in heparinized saline. The number of infiltrating cells were determined using a coulter counter. The inflammatory mediators prostaglandin $E_2$, $LTB_4$ and $TxB_2$ in the exudate were determined by radioimmunoassay.

The results of the effect of Compound 1, indomethacin and BW755C on cell infiltration and mediator production is shown in Table II. Compound 1 dosed at 1% and 5% reduced cell infiltration by 36.1 and 96.1% respectively. In contrast indomethacin at 1% did not significantly reduce cell infiltration. BW755C dosed at 5% reduced cell infiltration by 79%. All of the treatments reduced the concentrations of mediators in the exudate.

TABLE

| Treatment | Leukocyte No. cells/ml ($\times 10^{-6}$) | ng/ml Exudate | | |
|---|---|---|---|---|
|  |  | $PGE_2$ | $TXB_2$ | $LTB_4$ |
| Experiment 1 |  |  |  |  |
| Control (0.5% Carrageenan) | 10.8 ± 1.5 | 10.8 ± 3.7 | 3.6 ± 1.3 | 11.8 ± 4.1 |

TABLE-continued

| Treatment | Leukocyte No. cells/ml (× 10⁻⁶) | ng/ml Exudate PGE$_2$ | TXB$_2$ | LTB$_4$ |
|---|---|---|---|---|
| Compound 1 (0.5% Carrageenan plus 1% Compound 1) | 6.9 ± .7 | 5.7 ± 0.9 | 0.3 ± 0.1 | 2.1 ± 1.0 |
| Indomethacin (0.5% Carrageenan plus 1% Indomethacin) | 8.4% ± 1.7 | 1.9 ± 0.3 | <0.5 | 1.6 ± 0.5 |
| Experiment 2 | | | | |
| Control (0.5% Carrageenan) | 33.0 ± 3.8 | 137.6 ± 13.1 | 19.2 ± 1.9 | 5.5 ± 0.9 |
| Example (0.5% Carrageenan plus 5% Compound 1) | <1 | 21.3 ± 4.1 | 4.1 ± 0.9 | 2.4 ± 0.9 |
| BW755C (0.5% Carrageenan plus 5% BW755C) | 6.9 ± 1.7 | 3.0 ± 1.0 | 0.8 ± 0.3 | N.D. |

These results indicate that the compounds of the present invention can reduce cellular infiltration and mediator production in an in vivo system. Since cell infiltration is a characteristic of many inflammatory conditions, the compounds of the present invention are useful in treating inflammatory disease.

Subsequent to synthesizing and testing the compounds of Formula 1, further work was carried out to explore the effect of substituting the phenyl moiety of the compounds of Formula I with a wide range of substituents. As a result of this work it has been found that the phenyl-substituted compounds of general Formula II below have comparable activity to the unsubstituted compounds of Formula I.

Thus, in a further aspect of the present invention, there are provided the compounds of the formula

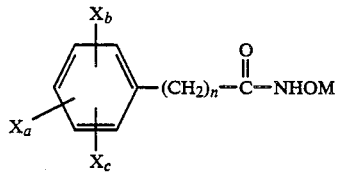

II wherein n is an integar of from six to eleven; M is hydrogen or a pharmaceutically acceptable cation; $X_a$, $X_b$ and $X_c$ each independently represent hydrogen, (lower)alkyl, (lower)alkenyl, (lower)alkoxy, halo (chloro, bromo, iodo or fluoro), nitro, hydroxy, amino, cyano, thio, optionally substituted aryl, optionally substituted aryl(lower)alkyl, (lower)alkylthio, acyl, acyloxy, acylamino, cycloalkyl having from 3 to 6 carbons, cycloalkyloxy wherein the cycloalkyl group has from 3 to 6 carbons, (lower)alkylamino or di(lower)alkylamino, providing that $X_a$, $X_b$ and $X_c$ are not all hydrogen.

In addition, compounds of general Formula III below have been synthesized which are N-alkylhydroxamic acid derivatives of the compounds of Formulae I and II. Surprisingly, the compounds of Formula III have been found to have dramatically increased lipoxygenase inhibitory activity relative to the corresponding hydroxamic acid compounds.

The present invention, therefore, provides compounds of the formula

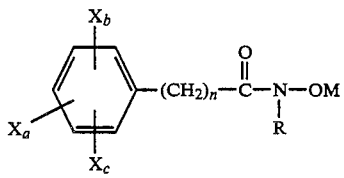

III wherein n is an integer from six to eleven; M is hydrogen or a pharmaceutically acceptable cation; R is $C_1$ to $C_6$ alkyl optionally substituted by a carboxyl group; and $X_a$, $X_b$ and $X_c$ each independently represent hydrogen, (lower)alkyl, (lower)alkenyl, (lower)alkoxy, halo, nitro, hydroxy, amino, cyano, thio, optionally substituted aryl, optionally substituted aryl(lower)alkyl, (lower)alkylthio, acyl, acyloxy, acylamino, cycloalkyl having from 3 to 6 carbons, cycloalkyloxy wherein the cycloalkyl group has from 3 to 6 carbons, (lower)alkylamino or di(lower)alkylamino.

The term "(lower)alkyl" as employed herein by itself or as part of another group includes, with respect to the X substituent of the compounds of Formula III, both straight and branched chain hydrocarbon radicals of up to six carbons and, with respect to the X substituent of the compounds of Formula II, both straight and branched chain hydrocarbon radicals of up to four carbons. The term "(lower)alkyl" when it refers to substituent R means straight or branched chain hydrocarbon radicals of up to six carbons.

The term "(lower) alkenyl" as employed herein to define substituents X in Formula III means straight or branched chain alkenyl radicals of from 2 to 6 carbons or, in the case of substituents X in the compounds of Formula II, alkenyl radicals of from 2 to 4 carbons.

The term "aryl" as employed herein by itself or as part of another group refers to monocyclic or bicyclic aromatic groups containing from 6 to 10 carbons in the ring portion such as phenyl or naphthyl. A preferred aryl group is phenyl. The term "optionally substituted aryl" means that the aryl ring may be substituted, preferably by one to three, more preferably one or two, and most preferably one substituent independently selected from $C_1$ to $C_4$ alkyl, halo, $C_1$ to $C_4$ alkoxy, nitro, hydroxyl, $C_1$ to $C_4$ alkylamino, di($C_1$ to $C_4$)alkylamino, cyano, $C_1$ to $C_4$ alkanoyl, $C_1$ to $C_4$ alkanoylamino, amino or $C_1$ to $C_4$ alkylthio substituents.

The term "acyl" as used herein by itself or as part of another group means a group of the formula

wherein $R_1$ is hydrogen, $C_1$ to $C_4$ alkyl, $C_2$ to $C_4$ alkenyl, $C_6$ to $C_{10}$ aryl, $C_6$ to $C_{10}$ aryl(lower)alkyl, heteroaryl or heteroaryl($C_1$ to $C_4$)alkyl wherein the hetero atom or atoms in the above-named heterocyclic moieties are selected from the group consisting of O, N or S atoms and preferably have 5- or 6-membered rings. A most preferred acyl group is $C_1$ to $C_4$ alkanoyl. Acyl includes also substituents in which the $R_1$ moiety is substituted by one or more halogen atoms.

A preferred group of compounds within those encompassed by Formula II comprises those in which n is 7, 8 or 9. A most preferred group consists of those in which n=8.

The phenyl ring of the compounds of Formula II is substituted by one, two or three substituents selected from those defined above. Preferably the phenyl ring has 1 or 2, most preferably one, non-hydrogen substituent.

One preferred group of compounds of Formula II comprises those compounds in which $X_a$, $X_b$ and $X_c$ each independently represent hydrogen, $C_1$–$C_4$ alkyl, $C_2$–$C_4$ alkenyl, halo, nitro, hydroxy, amino, thio, acyl or $C_1$–$C_4$ alkoxy, providing that $X_a$, $X_b$ and $X_c$ may not all be hydrogen.

Another preferred group of compounds of Formula II comprises those compounds in which $X_a$, $X_b$ and $X_c$ each independently represent hydrogen, $C_1$–$C_4$ alkylamino, acylamino, acyloxy or $C_1$–$C_4$ alkylthio; providing that $X_a$, $X_b$ and $X_c$ may not all be hydrogen.

Another preferred group of compounds of Formula II comprises those compounds in which $X_a$, $X_b$ and $X_c$ each independently represent hydrogen, cyano, phenyl, substituted phenyl, phenyl($C_1$–$C_4$)alkyl, $C_1$–$C_4$ alkylthio, $C_{3–6}$ cycloalkyl or $C_{3–6}$ cycloalkyloxy, providing that $X_a$, $X_b$ and $X_c$ may not all be hydrogen.

A most preferred group of compounds of Formula II comprises those compounds in which $X_a$, $X_b$ and $X_c$ each independently represents hydrogen, halo, $C_1$–$C_4$ alkyl or $C_1$–$C_4$ alkoxy, providing that $X_a$, $X_b$ and $X_c$ may not all be hydrogen.

With respect to the compounds of Formula III, the preferred compounds are those where n=7, 8 or 9, most preferably 8. The phenyl ring is preferably unsubstituted or substituted by one, two or three, preferably one or two and most preferably one, non-hydrogen substituent.

One preferred group of compounds of Formula III are those in which $X_a$, $X_b$ and $X_c$ are each hydrogen.

Another preferred group of compounds of Formula III comprises the compounds in which $X_a$, $X_b$ and $X_c$ each independently represent hydrogen, $C_1$–$C_6$ alkyl, $C_2$–$C_6$ alkenyl, halo, nitro, hydroxy, amino, thio, acyl or $C_1$–$C_6$ alkoxy, providing that $X_a$, $X_b$ and $X_c$ may not all be hydrogen.

Another preferred group of compounds of Formula III comprises the compounds in which $X_a$, $X_b$ and $X_c$ each independently represent hydrogen, $C_1$–$C_6$ alkylamino, acylamino, acyloxy or $C_1$–$C_6$ alkylthio; providing that $X_a$, $X_b$ and $X_c$ may not all be hydrogen.

Another preferred group of compounds of Formula III comprises the compounds in which $X_a$, $X_b$ and $X_c$ each independently represent hydrogen, cyano, phenyl, substituted phenyl, phenyl($C_1$–$C_6$)alkyl, $C_1$–$C_6$ alkylthio; $C_{3–6}$ cycloalkyl or $C_{3–6}$ cycloalkyloxy, providing that $X_a$, $X_b$ and $X_c$ may not all be hydrogen.

A most preferred group of compounds of Formula III comprises those compounds in which $X_a$, $X_b$ and $X_c$ each independently represents hydrogen, halo, $C_1$–$C_6$ alkyl or $C_1$–$C_6$ alkoxy, providing that $X_a$, $X_b$ and $X_c$ may not all be hydrogen.

The compounds of Formulae II and III may be prepared by the same general procedures as described above for preparation of compounds I. In the case of the N-alkylhydroxamic acid derivatives of Formula III, the phenylalkyl carboxylic acid is converted to an activated acid derivative such as the acid halide and then this derivative is condensed with a substituted hydroxylamine of the formula

wherein R is $C_1$–$C_6$ alkyl optionally substituted by a carboxyl group to give the desired end product.

In addition to providing the novel compounds of Formulae I–III, the present invention provides a method of inhibiting 5-lipoxygenase activity in a mammal (human or lower animal host) in need of such treatment, which method comprises administering to said mammalian host an amount of a compound of Formula I, II or III effective to inhibit lipoxygenase activity in the host. The compounds may be administered orally, parenterally or topically in dosage unit formulation containing conventional pharmaceutically acceptble carriers.

Also provided is a method of preventing or treating inflammation in a mammalian host, which method comprises administering to a host in need of such treatment a therapeutically effective amount of a compound of Formula I, II or III. The compound may be administered orally, parenterally or topically, The term "parenteral" as used herein includes intravenously, intramuscularly and subcutaneously. The term "topical" as used herein includes administration rectally and by inhalation spray as well as by the more common routes of the skin and the mucous membranes of the mouth and nose.

Total daily dose of the compounds of the invention administered to a host in single or divided dose may be in amounts of from about 0.001 to 2000 mg/kg body weight daily and more generally about 0.01 to 10 mg/kg/day. Dosage unit compositions may contain such amounts or such submultiples thereof as may be used to make up the daily dose. It will be understood, however, that the specific dose level for any particular patient will depend upon a variety of factors including the activity of the specific compound administered, the age, body weight, sex, diet, time and route of administration, rates of absorption and excretion, combination with other drugs and the type and severity of disease being treated.

Also provided by the present invention are pharmaceutical compositions in unit dosage form for the inhibition of 5-lipoxygenase activity in a mammalian host in need of such treatment, comprising an effective amount of a compound of Formula I, II or III and one or more pharmaceutically acceptable carriers.

Pharmaceutical compositions in unit dosage form for the treatment or prevention of inflammation in mammals are also provided, said compositions comprising a therapeutically effective amount of compound of Formula I, II or III and one or more pharmaceutically acceptable carriers.

A variety of materials can be used as carriers in the pharmaceutical compositions of the present invention. Injectable preparations, such as sterile injectable aqueous or oleaginous solutions, suspensions or emulsions, may be formulated according to known methods, using suitable dispersing or wetting agents and suspending agents, as needed. The sterile injectable preparation may employ a nontoxic parenterally acceptable diluent or solvent as, for example, sterile nonpyrogenic water or 1,3-butanediol. Among the other acceptable vehicles and solvents that may be employed are 5% dextrose injection, Ringer's injection and isotonic sodium chloride injection (as described in the USP/NF). In addition, sterile fixed oils are conventionally employed as solvents or suspending media. For this purpose any bland fixed oil may be used including synthetic mono-, di- or triglycerides. Fatty acids such as oleic acid can also be used in the preparation of injectable compositions.

Suppositories for rectal administration can be prepared by mixing the drug with suitable nonirritating excipients such as cocoa butter and polyethylene glycols which are solid at ordinary temperatures but liquid at body temperature and which therefore melt in the rectum and release the drug.

Solid dosage forms of oral administration include capsule, tablets, pills, troches, lozenges, powders and granules. In such solid dosage forms, the active compound may be admixed with at least one inert diluent such as sucrose, lactose or starch. Such dosage forms may also comprise, as is normal practice, pharmaceutical adjuvant substances, e.g., stearate lubricating agents. In the case of capsules, tablets and pills, the dosage forms may also contain buffering agents. Solid oral preparations can also be prepared with enteric or other coatings which modulate release of the active ingredients.

Liquid dosage forms for oral administration include pharmaceutically acceptable emulsions, solutions, suspensions, syrups and elixirs containing inert nontoxic diluents commonly used in the art such as water and alcohol. Such compositions may also comprise adjuvants, such as wetting agents, emulsifying suspending, sweetening, flavoring and perfuming agents.

As noted above 5-lipoxygenase products are involved in a number of inflammatory and allergic disease states and thus, the compounds of the present invention are useful in the treatment of such disease states. The treatment of psoriasis and other inflammatory and allergic dermatological disorders is a preferred embodiment of the invention.

The following examples illustrate the synthesis of starting materials and products of the present invention.

PREPARATION OF STARTING MATERIALS

PROCEDURE 1

Preparation of 12-Phenyldodecanoic Acid via Cyclic Anhydride Route

A. 1,10-Decanedicarboxylic Anhydride

A starting mixture of 23 gms (0.1 mole) of 1,10-decanedicarboxylic acid and 18 gms (0.1 mole) of acetic anhydride was refluxed for 18 hours and then concentrated in vacuo to remove acetic acid and excess acetic anhydride. The residue was dissolved in 300 ml methylene chloride, filtered, washed with ice-cold 5% sodium bicarbonate solution, water, and saturated sodium chloride. After the final separation of the layers, the organic solution was dried over $MgSO_4$, filtered, and evaporated in vacuo to give 20 gms crude product. This was purified by dissolving it in 100 ml boiling methylene chloride, filtering hot, diluting with 200 ml hexanes, and refrigerating. This resulted in 13 gms pure title product m.p. 85°-9°.

B. 11-Benzoylundecanoic Acid

To a stirred suspension of 18 gms $AlCl_3$ (0.135 mole) in 150 ml dry benzene was added 13 gms 1,10-decanedicarboxylic anhydride in small portions over 15 minutes, then the mixture was refluxed for 6 hours. The solid was filtered off, stirred for 2.5 hours in 350 ml 2N HCl, removed by filtration, and stirred in 300 ml 1N NaOH which was then heated to 70° and filtered hot. As the solution cooled, solid material (sodium salt of the product) crystallized out. This salt was dissolved in hot water, acidified to pH 3 with concentrated HCl, filtered after cooling, and dried to give 5.5 gm of the desired 11-benzoylundecanoic acid m.p. 83°-6°.

C. 12-Phenyldodecanoic Acid

To a solution of 1 gm $Hg_2Cl_2$ in 30 ml $H_2O$ was added 1 ml of concentrated HCl followed by 24 gms powdered Zn (portion wise) with mechanical stirring. The resulting mixture was stirred together for 5 minutes, then the liquid phase was decanted off, and 15 ml $H_2O$ was added, followed by 36 ml concentrated HCl. This mixture was cooled to room temperature (the reaction to this point is exothermic), then 5.4 gms 11-benzoylundecanoic acid was added followed by 25 ml toluene. The resulting mixture was stirred and refluxed for 20 hours; 12 ml concentrated HCl was added during the first 6 hours of the reflux. The reaction mixture was cooled, the liquid was decanted, the phases were separated and the solid was three times triturated with 25 ml ether. The aqueous phase was 3×15 ml ether extracted; all organic phases were combined, washed with water and brine and dried over $MgSO_4$. The drying agent was filtered off, and the solvents were removed in vacuo to give a solid residue. This residue was dissolved in ether, extracted with dilute NaOH, and the organic layer was discarded. The aqueous layer was acidified with concentrated HCl, then extracted with ether. This ether solution was washed with water and brine, dried over $MgSO_4$, filtered, and evaporated in vacuo to give 4.2 gms title product which was used without further purification.

PROCEDURE 2

Preparation of 12-Benzoyldodecanoic Acid by Half-acid/Half-ester Route

A. Dimethyl 1,11-Undecanedicarboxylate

To a mixture of 6.5 gms 1,11-undecanedicarboxylic acid and 125 ml $CH_3OH$ was added 1 ml concentrated $H_2SO_4$ and 5 gms 3 A molecular sieves. This mixture was refluxed for 18 hours, cooled to room temperature, and then solid $NaHCO_3$ was added in small portions (foaming). The resulting mixture was filtered and evaporated in vacuo. The residue was dissolved in a mixture of 200 ml $CH_2Cl_2$ and 30 ml water. The mixture was shaken in a separatory funnel, the organic layer was separated, washed with 5% $NaHCO_3$ solution, water, then brine, dried over $MgSO_4$, filtered, and evaporated in vacuo to give 6.4 gms of low-melting solid which was used directly in the next step.

B. Monomethyl 1,11-Undecanedicarboxylate

To a stirred solution of 6.4 gms dimethyl 1,11-undecanedicarboxylate in 200 ml CH₃OH was added a solution of 1.3 gms KOH in 10 ml H₂O and the resulting mixture was stirred at room temperature overnight. The solvent was removed in vacuo and the residue was triturated with 100 ml H₂O. The water-insoluble material was dissolved in ether, determined to be starting material, and was recycled. The aqueous solution was made acidic to pH 3 and the precipitated solid filtered and dried to give 3.4 gms title product with m.p. 85°–90°. Another 1.6 gms was recovered from the recycled starting material.

C. 12-(Methoxycarbonyl)dodecanoyl Chloride

To a cold solution of 4.8 gms monomethyl 1,11-undecanedicarboxylate in 10 ml $CH_2Cl_2$ was added 5 ml $SOCl_2$ dropwise over 5 minutes; then it was stirred at room temperature for 18 hours. The solvent was removed in vacuo to give 4.8 gms of an oily residue which was used without further purification.

D. Methyl(12-Benzoyl)dodecanoate

To a stirred suspension of 3 gms AlCl₃ in 15 ml dry benzene at 40° was added the acid chloride from the previous step. The resulting mixture was refluxed for 2 hours, then cooled and poured over 200 ml ice containing 15 ml concentrated HCl. After stirring for 1½ hours the aqueous mixture was extracted 3×50 ml $CH_2Cl_2$. The organic phases were combined, washed with water, 5% NaHCO₃, brine, and dried over MgSO₄. The drying was filtered off and the solvent was removed in vacuo to give 4.5 gms yellow oil whose IR spectrum showed two C=O peaks plus the presence of aromatic C—H bonds. This oil was hydrolyzed directly in the next step. E. 12-Benzoyldodecanoic Acid A mixture of 4.5 gms crude ester from the previous step, 20 ml CH₃OH, and 30 ml of H₂O containing 2 gms NaOH was refluxed for 4 hours and cooled to room temperature. The solvent was removed in vacuo and triturated with a little cold water. The solid was filtered, washed with a little 1:1 ether:hexane mixture, and dissolved in hot water. The hot solution was acidified with concentrated HCl and the precipitate collected by filtration. The solid was purified by column chromatography in $CH_2Cl_2$ over 50 gms silica gel.

Ten fractions of 30 ml each were collected and discarded, then the eluting solvent was charged to 10% EtOAc/$CH_2Cl_2$ and the next 23 fractions were collected and combined, corresponding to the third major component. The solvents were removed in vacuo to give 0.7 gm yellow oil whose IR showed an acid O—H and two C=O stretching bonds between 1680–1720 cm$^{-1}$. The NMR showed the expected aromatic and aliphatic signals. This product was reduced as described above to give 13-phenyl-tridecanoic acid.

EXAMPLES

EXAMPLE 1

Preparation of 9-Phenylnonanohydroxamic Acid

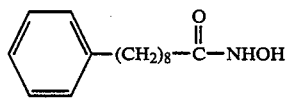

Into a 100 ml, 3 neck flask equipped with thermometer, drying tube, stirrer and dropping funnel is placed phenylnonanoic acid (10 gms, 0.0426 mole) and methylene chloride (20 ml). The resulting stirred mixture is cooled to 5° and thionyl chloride (6.2 gms, 0.052 mole) is added dropwise during 5 minutes, then stirred at room temperature for 18 hours. The methylene chloride and excess thionyl chloride are removed in vacuo to an oil, 10.8 gms (100%). This is diluted with methylene chloride (15 ml) and then added to a stirred mixture of hydroxylamine hydrochloride (3.6 gms, 0.052 mole), anhydrous sodium carbonate (5 gms, 0.052 mole) and methylene chloride (60 ml). During the addition, the temperature of the reaction is maintained between 5°–10° by regulating the addition. After stirring this mixture for ½ hour, water (6 ml) is added dropwise during 5 minutes, then the mixture is stirred at room temperature for 18 hours. The reaction mixture is diluted with methylene chloride (60 ml) and water (30 ml). The organic layer is separated and washed with water (2×30 ml), brine (2×30 ml), and dried over magnesium sulfate, then filtered and concentrated in vacuo to a solid residue. One recrystallization from methylene chloride (100 ml) gives 6.7 gms (63%) of pure title product, m.p. 75°–7°.

EXAMPLE 2

Following the general procedure of Example 1, the following compounds were prepared from the appropriate phenylalkyl carboxylic acid starting materials:

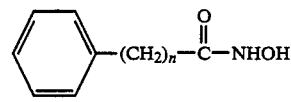

| Compound | n | m.p. | Elemental Analysis |
|---|---|---|---|
| 2a | 6 | 64–66° C. | C,H,N |
| 2b | 7 | 79–81° C. | C,H,N |
| 2c | 9 | 77–79° C. | C,H,N |
| 2d | 10 | oil | * |
| 2e | 11 | 88–91° C. | C,H,N |

*Calculated C 73.60 H 9.81 N 5.05
Found C 73.30 H 9.88 N 4.44

EXAMPLE 3

N-Alkylhydroxamic Acids

A. Acid Chloride Synthesis

8-Phenyloctanoyl Chloride

In a 50 ml round bottom flask equipped with drying tube and stirrer were placed 7.33 gms (0.033 moles) 8-phenyloctanoic acid and 23 ml thionyl chloride, after which a condenser was attached to the flask. The mixture was then refluxed for 2 hrs, cooled to room temperature, and the thionyl chloride was removed in vacuo to give the crude acid chloride, which was used without further purification in the next step. Yield 7.97 gm.

By the above method were also prepared the following:
4-phenylbutanoyl chloride
5-phenylpentanoyl chloride
7-phenylheptanoyl chloride
9-phenylnonanoyl chloride
10-phenyldecanoyl chloride
15-phenylpentadecanoyl chloride B. N-alkylhydroxamic acid synthesis N-methyl-8-phenyloctanohydroxamic acid In a 250 ml 3-neck round bottom flask equipped with stirrer and drying tube were placed 2.68 gm N-methyl hydroxylamine hydrochloride, 3.09 gms anhydrous sodium carbonate and 80 ml $CH_2CL_2$. The stirred mixed was cooled in an ice bath and 5.9 gm 8-phenyloctanoyl chloride were added over 10 minutes. After ½ hr stirring in the cold, 7.5 ml water was added, and the resulting mixture was stirred at room temperature overnight. To the reaction mixture was then added 50 ml water, the organic layer was separated, and the water layer was 2×25 ml $CH_2CL_2$ extracted. All organic fractions were combined, washed 2×25 ml water and 2×20 ml saturated aqueous NaCl, and dried over $MgSO_4$. The drying agent was removed by filtration and the solvent was removed in vacuo. The resulting oil was dissolved in 5 ml ethyl acetate and passed down a 50 gm silica gel column. The material was recrystallized from a mixture of 3:1 hexanes: $CH_2Cl_2$ after charcoal treatment to give 1.24 gm product of melting point 35.5°–7° C. Elemental analysis: calculated C 72.25, H 9.30, N 5.62, O 12.83%. Found C 72.16, H 9.40, N 5.56%.

By the above method were prepared the following compounds:

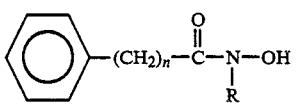

| n | R | crystallization solvent | Yield (%) | m.p. (°C.) | BMY |
|---|---|---|---|---|---|
| 3 | $CH(CH_3)_2$ | Hexanes/$CHCl_3$ | 47 | 54.5–5.5 | 30227[1] |

-continued

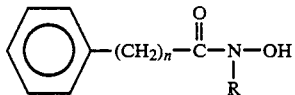

| n | R | | | | |
|---|---|---|---|---|---|
| 4 | $CH(CH_3)_2$ | Hexanes | 37 | 48.5–9 | 30226 |
| 6 | $CH(CH_3)_2$ | Hexanes | 43 | 54–6 | 30222[1,2] |
| 7 | $CH_3$ | Hexanes/$CHCl_2$ | 20 | 35.5–7 | 30208 |
| 7 | $CH(CH_3)_2$ | Hexanes ($2^2$x) | 33 | 40–2 | 30214[1] |
| 8 | $CH_3$ | Hexanes | 68 | 35.5–7 | 30223 |
| 8 | $CH(CH_3)_2$ | Hexanes | 51 | 49.5–50.5 | 30224 |
| 9 | $CH_3$ | Hexanes | 47 | 46.5–8 | 30217 |
| 9 | $CH(CH_3)_2$ | Hexanes | 40 | 49–50 | 30218[1] |
| 14 | $CH_3$ | Hexanes | 34 | 71.5–2.5 | 30228[1] |
| 14 | $CH(CH_3)_2$ | Hexanes | 29 | 79.5–80 | 30229[1] |

Notes:
[1] Silica gel treatment not required
[2] Crystallization mixture twice washed with $NaHCO_3$ solution Elemental Analysis

| BMY | Calculated | | | | Found | | |
|---|---|---|---|---|---|---|---|
| | C | H | N | O | C | H | N |
| 30227 | 70.55 | 8.65 | 6.33 | 14.47 | 70.35 | 8.82 | 6.32 |
| 30226 | 71.45 | 9.00 | 5.95 | 13.60 | 71.07 | 9.07 | 5.79 |
| 30222 | 72.96 | 9.51 | 5.32 | 12.21 | 73.09 | 10.21 | 5.42 |
| 30208 | 72.25 | 9.30 | 5.62 | 12.83 | 72.16 | 9.40 | 5.56 |
| 30214 | 73.60 | 9.81 | 5.05 | 11.54 | 73.51 | 10.03 | 4.97 |
| 30223 | 72.96 | 9.51 | 5.32 | 12.21 | 73.04 | 9.85 | 5.45 |
| 30224 | 74.18 | 10.03 | 4.81 | 10.98 | 74.02 | 10.19 | 5.03 |
| 30217 | 73.60 | 9.81 | 5.05 | 11.54 | 73.49 | 10.07 | 5.07 |
| 30218 | 74.71 | 10.23 | 4.59 | 10.48 | 74.32 | 10.25 | 4.63 |
| 30228 | 76.03 | 10.73 | 4.03 | 9.21 | 75.92 | 11.03 | 4.01 |
| 30229 | 76.75 | 11.00 | 3.73 | 8.52 | 76.57 | 11.41 | 3.74 |

The enzyme inhibitory data, obtained by the procedure described previously, are given below.

FIG. 1

Inhibition of LPO/CO by BMY 30094 Analogues

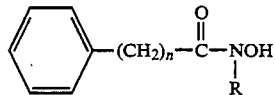

| Compound | a | R | IC50 (μM) (95% confidence interval) | | |
|---|---|---|---|---|---|
| | | | Human PMNL 5-LPO | Human Platelet CO | Human Platelet 12-LPO |
| BMY30077 | 3 | —H | 11% I @ 100 μM | | |
| BMY30227 | 3 | —isopropyl | 0.7 (0.3–1.5) | 7(±6)% I @ 100 μM | 31(±7)% I @ 100 μM |
| BMY30083 | 4 | —H | 22% I @ 100 μM | | |
| BMY30226 | 4 | —isopropyl | 0.9 (0.6–1.2) | 25(±5)% I @ 100 μM | 59 59(±8)% I @ 100 μM |
| BMY30089 | 6 | —H | 20.9 (10.1–43.1) | | |
| BMY30222 | 6 | —isopropyl | 0.07 (0.03–0.16) | 30.9 (21.0–44.8) | 12.5 (7.5–19.7) |
| BMY30116 | 7 | —H | 12.2 (9.6–14.7) | 26 | 53(±10)% I @ 100 μM |
| BMY30208 | 7 | —methyl | 0.10 (0.03–0.29) | 2.9 (1.6–5.1) | 3.6 (1.8–7.4) |
| BMY30214 | 7 | —isopropyl | 0.16 (0.06–0.41) | 4.2 (1.5–12.4) | 4.5 (2.4–9.1) |
| BMY30094 | 8 | —H | 5.7 (4.5–7.1) | 15 | 33(±3)% I @ 100 μM |
| BMY30223 | 8 | —methyl | 0.17 (0.10–0.28) | 2.1 (0.9–4.0) | 2.5 (1.8–4.2) |
| BMY30224 | 8 | —isopropyl | 0.18 (0.07–0.45) | 18.4 (13.0–23.4) | 13.9 (8.7–20.5) |
| BMY30096 | 9 | —H | 11.6 (7.9–18.0) | 32 | 10(±2)% I @ 100 μM |
| BMY30217 | 9 | —methyl | 0.09 (0.04–0.16) | 4.6 2.0–10.3) | 5.5 (3.1–9.7) |

FIG. 1-continued

Inhibition of LPO/CO by BMY 30094 Analogues

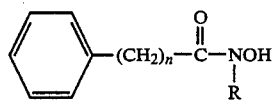

| Compound | a | R | Human PMNL 5-LPO | Human Platelet CO | Human Platelet 12-LPO |
|---|---|---|---|---|---|
| BMY30218 | 9 | —isopropyl | 0.14 (0.04–0.37) | 7.6 (2.9–20.9) | 26.7 (14.7–53.4) |
| BMY30152 | 14 | —H | 7.5% I @ 50 µM | | |
| BMY30228 | 14 | —methyl | 25.3 (18.0–33.8) | inactive @ 100 µM | 17(±8)% I @ 100 µM |
| BMY30229 | 14 | —isopropyl | 80.0 (40–181) | inactive @ 100 µM | 10(±5)% I @ 100 µM |

IC50 (µM) (95% confidence interval)

General Method

Step 1

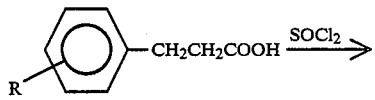

Step 2

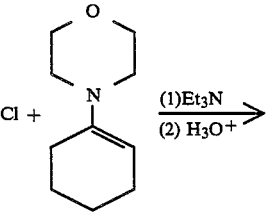

Step 3

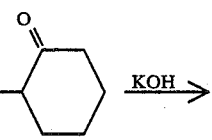

Step 4

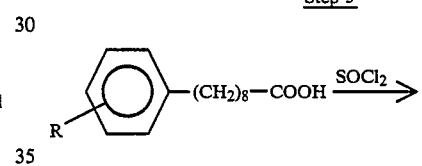

-continued
General Method

Step 5

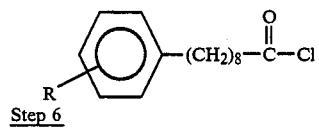

Step 6

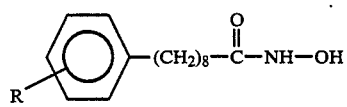

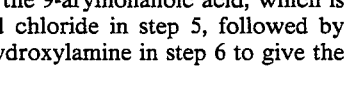

In step 1, a 3(substituted phenyl)propionic acid is converted to the acid chloride with thionyl chloride. This is then condensed in step 2 with 1-morpholinocyclohexene to give the 2(3-arylpropionyl)cyclohexanone. In step 3, the cyclohexanone is cleaved with base (retro-Dieckmann reaction) to give a 9-aryl-7-ketononanoic acid. A Wolff-Kishner reduction in step 4 converts this acid to the 9-arylnonanoic acid, which is converted to its acid chloride in step 5, followed by condensation with hydroxylamine in step 6 to give the desired product.

PROCEDURE

Step 1

3-[4-Chlorophenyl)propionyl chloride

To a stirred, ice-cold suspension of 3(4-chlorophenyl)propionic acid in 25 ml CH$_2$Cl$_2$ was added dropwise over 5 minutes 5.4 ml of thionyl chloride. The solution was allowed to warm up to room temperature and was stirred for 72 hrs. The solvent and excess thionyl chloride were removed in vacuo to give the crude product as an oil (10.2 gm crude yield), which was used directly in the next step without purification.

Also prepared by this procedure were:
3(3-methylphenyl)propionyl chloride
3(4-methoxyphenyl)propionyl chloride (reacted only 18 hrs)
3(3-methoxyphenyl)propionyl chloride (reacted only 18 hrs)

Step 2

2(3(4'-chlorophenyl)propionyl)cyclohexanone

To a stirred, ice-cold solution of 5.7 gms 1-morpholinocyclohexane and 5.9 ml triethylamine in 20 ml $CH_2Cl_2$ was gradually added a solution of 8.7 gm 3(4-chlorophenyl)propionyl chloride in 20 ml $CH_2Cl_2$. The temperature was kept below 10° C. during the addition. The mixture was then allowed to warm up to room temperature and was stirred overnight. 17 ml of 18% HCl solution was gradually added to the reaction mixture and the mixture was refluxed for 5 hours. The reaction mixture was then cooled, diluted with more $CH_2Cl_2$, and washed three times with water and once with saturated NaCl solution. The organic layers were separated, driied over $MgSO_4$, filtered, the solvents removed in vacuo, and the resulting oil vacuum distilled. (Sublimation of an impurity fraction required interruption of the distillation to clear the column.) The main fraction distilled at 175°–80° C. at 0.75 mm. This product (yellow oil) was used without further purification in step 3.

Also prepared by this procedure were:
2(3(3'-methyl phenyl)propionyl)cyclohexanone, b.p. 150°–159° at 0.75 mm ($CHCl_3$ used as solvent).
2(3(4'-methoxyphenyl)propionyl)cyclohexanone (used without distillation).
2(3(3'-methoxyphenyl)propionyl)cyclohexanone (used without distillation).

Step 3

9(4-chlorophenyl)-7-ketononanoic acid

A mixture of 6.9 gm 2(3(4'-chlorophenyl)propionyl)-cyclohexanone and 33 ml 4N KOH was refluxed for 1 hour, cooled, and three times extracted with ether. The organic fractions were discarded. The aqueous solution was acidified with conc. HCl, upon which a white precipitate formed. The mixture was placed in the cold overnight, then the solid was filtered off, washed with cold water, and dried with a vacuum pump. Yield 5.4 gms (73%) white solid m.p. 93°–6° C.

Also prepared by this method was
9(4-methoxyphenyl)-7-ketononanoic acid (m.p. 73°–5°)
9(3-methylphenyl)-7-ketonanoic acid To 30 ml of a refluxing 4N KOH solution was added 7.8 gms 2(3(3'-methylphenyl)propionyl)cyclohexanone. The resulting mixture was refluxed for 30 min and cooled to room temperature. It was washed three times with ether (organic phase discarded) and acidified with conc. HCl whereupon two layers found. The organic phase was extracted with three portions of $CHCl_3$. The chloroform was combined and washed twice with water and once with saturated NaCl solution. The organic layer was dried over $MgSO_4$, filtered, and evaporated in vacuo. On cooling for 2 hrs in the cold and drying over 72 hrs on a vacuum pump, 84% of the desired product, m.p. 41°–4° C. was obtained.

9(3-methoxyphenyl)-7-ketononanoic acid

A mixture of 8.3 gms 2(3(3-methoxyphenyl)propionyl)-cyclohexanone and 40 ml 4N KOH solution was refluxed for 1 hr and then cooled to room temperature. It was diluted with more water, 6×20 ml ether extracted, then diluted with conc. HCl, whereupon an oil came out. The mixture was diluted with $CHCl_3$, and the organic layer was separated, washed twice with water and once with saturated NaCl solution. It was then dried over $MgSO_4$, filtered, and evaporated in vacuo to give an oil which was redissolved in 10% KOH, shaken with decolorizing charcoal, filtered through diatomaceous earth, and acidified with conc. HCl. The oil was taken up into $CHCl_3$, the $CHCl_3$ was washed twice with water and once with saturated NaCl solution and dried over $MgSO_4$. The drying agent was filtered off and the solvent was removed in vacuo. The resulting oil was dissolved in 300 ml of 1:1 ethyl acetate:chloroform, stirred with 60 gms silica gel, filtered, and the solvents removed in vacuo to give a brown oil, which was used directly in the next step without further purification.

Step 4

9(4-methoxyphenyl)nonanoic acid

To a stirring solution of 7.5 gms 9(4-methoxyphenyl)-7-ketononanoic acid in 35 ml diethylene glycol was added 5.1 ml hydrazine hydrate. The mixture was heated to 120° for 4 hrs, cooled to room temperature, connected to a water aspirator, and gently heated to 120° to remove excess water and hydrazine. The reaction mixture was cooled to 70°, 7.2 gm KOH was added, and the mixture was heated up to 220° C. where it was kept for 5 hr, then cooled. The cooled reaction mass was dissolved in 120 ml hot water, acidified with conc. HCl, and 3× extracted with $CHCl_3$. The combined organic phases were dried over $MgSO_4$, filtered, and the solvent was evaporated in vacuo. Attempts to crystallize the product failed, so it was vacuum sublimed twice, dissolved in 300 ml chloroform, filtered through silica gel, and the solvent evaporated to give 38% product, a white solid of m.p. 41°–3° C.

9(3-methylphenyl)nonanoic acid

To a stirred solution of 66 gm 9(3-methylphenyl)-7-ketononanoic acid in 35 ml diethylene glycol was added 4.3 ml hydrazine hydrate. The reaction mixture was heated at 120° for 5 hrs, cooled to 70° C., connected to a water aspirator, and re-heated to 120°–30° for 3½ hrs. The mixture was then cooled to 70°, 6.5 g KOH was added, and the reaction mixture was heated to 160°–200° (temperature varied with $N_2$ evolution) for 11 hr, then cooled to room temperature. The solidified reaction mass was dissolved in 150 ml hot water, acidified with conc. HCl, three times extracted with $CHCl_3$ and the organic phases were combined. They were washed three times with water, once with saturated NaCl solution, dried over $MgSO_4$, filtered, treated with charcoal, filtered through diatomaceous earth, and the solvent was removed in vacuo to give a brown oil which was vacuum distilled. Yield 61%. The main fraction boiled at 170°–80° at 0.1 mm and later solidified to a product of m.p. 39°–40°. Elemental analysis: calculated C 77.37, H 9.74. Found: C 77.25, H 9.98.

9(4-chlorophenyl)nonanoic acid

To a solution of 3.4 gms KOH in 23 ml diethylene glycol was added 5.4 gms 9(4-chlorophenyl)-7- ketononanoic acid and 3 ml hydrazine hydrate. The resulting mixture was heated at 145° for 1 hour. The mixture was cooled, attached to a water aspirator, and the excess water and hydrazine distilled off. The mixture was then re-heated to 145° for 3 hours and cooled. The oily reaction mixture was diluted with water, acidified with conc. HCl, and the precipitated solid filtered off. Since the NMR showed starting material still present, the solid was dissolved in 25 ml diethylene glycol and 4.1 ml hydrazine hydrate was added. This solution was refluxed for 3 hr, then the water and hydrazine were distilled off under vacuum as before. 5.2 gms KOH was added and the resulting mixture was heated at 160° for 3.5 hours, then cooled to room temperature overnight. It was dissolved in water and acidified with conc. HCl. The precipitated solid was dissolved in 10% KOH solution, washed three times with ether, filtered, acidified with conc. HCl, and placed in the cold overnight. The solid was filtered off, dried and recrystallized from hexanes to give 3.1 gm white solid of m.p. 73°–5° C.

9(3-methoxyphenyl)nonanoic acid

To a stirred solution of 9.3 gms 9(3-methoxyphenyl)-7-ketononanoic acid in 60 ml ethanol was added 6.7 ml hydrazine and the resulting mixture was refluxed for 18 hrs, then the excess hydrazine and the ethanol were removed in vacuo. The oil was then dissolved in freshly distilled dimethyl sulfoxide. To this was added 13 gm of potassium tert-butoxide and the resulting mixture heated at 100° for 18 hrs, cooled to room temperature, and poured into 300 ml ice-water. When the ice melted it was washed 3×40 ml ether, the aqueous phase acidified with conc. HCl to pH 3 and then extracted 4×60 ml ether. These ether extracts were combined, washed 2×25 ml water, 2×25 ml saturated NaCl solution, and dried over $MgSO_4$. The drying agent was removed by filtration and the ether was evaporated in vacuo to an oil which was dissolved in 200 ml $CHCl_3$ and stirred with 100 gms silica gel. The silica gel was filtered off (the $CHCl_3$ was discarded) and then extracted with 3×200 ml 10% ethyl acetate:$CHCl_3$ and 4×200 ml 25% ethyl acetate:$CHCl_3$. The solvents were evaporated and the residue applied to a 250 gm silica gel column (5 cm×40 cm) and the column was washed with 1 liter of $CHCl_3$, which was discarded, followed by 10% ethyl acetate:$CHCl_3$ with 40 ml fractions being collected. Fractions #8–24 were combined to give 2 gms of an oil, which was used in the next step without further purification.

Step 5

9(4-Methoxyphenyl)nonanoyl chloride

To an ice-cold, stirring solution of 3 gm 9(4-methoxyphenyl)nonanoic acid in 10 ml. $CH_2Cl_2$ was added dropwise 1.2 ml thionyl chloride. The solution was then allowed to warm up to room temperature. The solvent and excess thionyl chloride were removed in vacuo to give a brown oil, which was used directly in the last step without further purification.

Also prepared by this method was:
9(3-methylphenyl)nonanoyl chloride
9(3-methoxyphenyl)nonanoyl chloride
9(4-chlorophenyl)nonanoyl chloride Step 6

9(4-Methoxyphenyl)nonanohydroxamic acid

To a cold stirring suspension of 1 gm hydroxylamine hydrochloride and 1.3 gm sodium carbonate in 25 ml $CH_2Cl_2$ was added dropwise 1.58 gms 9(4-methoxyphenyl)nonanoyl chloride over a period of 15 min. The mixture was then stirred in the cold for a further 45 min, then 1.5 ml $H_2O$ was added, the mixture was allowed to warm up to room temperature, and stirring was continued for 72 hrs. The precipitated solid was filtered, washed with water, and crystallized twice from $CH_2Cl_2$ to give A. The filtrate from the reaction mixture was evaporated in vacuo to give a granular solid which was also crystallized twice from $CH_2Cl_2$ to give B. A and B were shown to be the same by spectral comparison. Total yield (A+B)=1.58 gm (51%) m.p. 96°–98° C. Elemental analysis: calculated C 67.90, H 8.90, N 4.95. Found C 67.96, H 9.08, N 4.95 (calculated for 0.2 moles $H_2O$).

9(4-chlorophenyl)nonanohydroxamic acid

To a cold, stirring suspension of 1 gm hydroxylamine hydrochloride and 1.2 gms sodium carbonate in 20 ml. $CH_2Cl_2$ was added dropwise 2.7 gms 9(4-chlorophenyl)nonanoyl chloride over 15 min, with the temperature maintained between 5°–10° C. After 45 min. stirring, 1.5 ml $H_2O$ was added, and the mixture was stirred at room temperature overnight. The mixture was diluted with $CH_2Cl_2$ and water, the layers were separated, and the organic layer was washed twice with water and once with NaCl solution. It was dried over $MgSO_4$, filtered, and the solvents removed in vacuo. The residue was crystallized from isopropyl ether, $CH_2Cl_2$:hexanes, and cyclohexane to give 0.12 gm white solid of m.p. 48°–50°. Elemental analysis: calculated (0.5 mole $H_2O$) C 62.50, H 7.76, N 4.85, Cl 12.29% found C 62.84, H 7.89, N 4.71, Cl 11.77%.

9(3-methylphenyl)nonanohydroxamic acid

To a cold, stirring suspension of 1.3 gm hydroxylamine hydrochloride and 1.8 gm sodium carbonate in 25 ml $CH_2Cl_2$ was added dropwise 4 gms 9(3-methylphenyl)nonanoyl chloride. The reaction mixture was stirred at 5°–10° for 45 min, then 2.1 ml $H_2O$ was added and the mixture stirred overnight at room temperature. The suspension was then diluted with $CH_2Cl_2$ and water, shaken, and the organic layer was separated. It was washed three times with water and once with NaCl solution, dried over $MgSO_4$, and filtered. The solvent was removed in vacuo to give an oil which solidified but which could not be crystallized. The solid was disolved in ether, shaken with 5% KOH, and the ether discarded. The aqueous layer was acidified and the precipitated solid extracted into $CHCl_3$. The chloroform was washed twice with water and once with NaCl solution, dried over $MgSO_4$, filtered, and evaporated in vacuo. The resulting oil was purified by silica gel column chromatography, using gradually increasing cocentrations of ethyl acetate in chloroform (0, 10%, 15%, 25%). Fractions containing the major component (detected by thin layer chromatography—Rf=0.4 in 1:1 ETOAc:$CHCl_3$) were collected and evaporated down to give an off-white solid which was crystallized from $CH_2Cl_2$:hexanes. Yield 1.3 gms (33%) product of m.p. 49°–50°. Elemental analysis: calculated C 72.98, H 9.57, N 5.32% found C 72.80, H 9.56, N 5.32%.

9(3-methoxyphenyl)nonanohydroxamic acid

To a cold stirred suspension of 0.7 gms hydroxylamine hydrochloride and 1 gm sodium carbonate in 10 ml $CH_2Cl_2$ was added a solution of 2.1 gms 9(3-methoxyphenyl)nonanoyl chloride in 10 ml $CH_2Cl_2$. After stirring this mixture for ½ hr, 1.1 ml $H_2O$ was added, and the reaction was stirred overnight at room temperature. 30 ml water was added, the layers were separated, and the aqueous layer 3×50 ml extracted with CH₂Cl₂. The organic phases were combined, washed 2×20 ml water, 2×20 ml NaCl solution, dried over MgSO₄, filtered, and evaporated in vacuo to give an oil which solidified on standing. The solid was crystallized from CH₂Cl₂:hexanes but was still impure by thin layer chromatography. It was dissolved in 100 ml CHCl₃, stirred with 20 gm silica gel, and filtered. The silica gel was suspended in 75 ml CHCl₃, stirred, and filtered (process repeated three times). All filtrates were combined, evaporated in vacuo, and the residue recrystallized from CH₂Cl₂:hexanes to give 0.7 gms product of m.p. 66°–8°. Elemental analysis: calculated C 68.79, H 9.02, N 5.01% found C 68.61, H 9.18, N 5.09%.

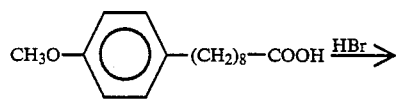

| X | BMY | IC₅₀(5-lipoxygenase) |
|---|---|---|
| 4-OCH₃ | 30173 | 2.4 μM |
| 4-Cl | 30174 | 6.1 μM |
| 3-OCH₃ | 30181 | 5.4 μM |
| 3-CH₃ | 30182 | 6.2 μM |
| H | 30094 | 5.7 μM (comparison) |

The activity was tested by the same method as in the previous example.

EXAMPLE 5

Preparation of 9(4-Alkoxyphenyl)nonanohydroxamic Acids

General Reaction Scheme

Step 1

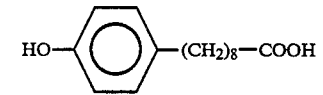

Step 2

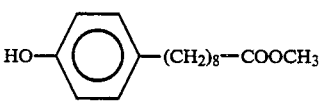

Step 3

(structure: HO—⟨⟩—(CH₂)₈—COOCH₃ →(1) R—Br (2) KOH)

(structure: R—O—⟨⟩—(CH₂)₈—COOH)

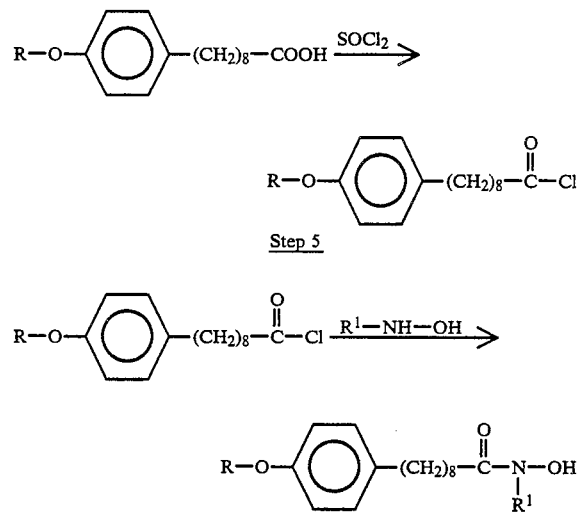

In step 1 of this synthetic sequence, the ether group of 9(4-methoxyphenyl)nonanoic acid is cleaved with hydrogen bromide to give the alcohol, 9(4-hydroxyphenyl)nonanoic acid. In step 2, this acid is converted to its methyl ester. In step 3, the 9(4-hydroxyphenyl)-nonanoic acid, methyl ester is alkylated (with n-butyl or n-hexyl bromide) and then hydrolyzed to give 9(4-alkoxyphenyl)nonanoic acids. In step 4, the acid is converted to the acid chloride, using thionyl chloride. In step 5, the acid chloride is condensed with a substituted or unsubstituted hydroxylamine to give the final product.

Step 1

9(4-Hydroxyphenyl)nonanoic acid

A mixture of 55.7 gms 9(4-methoxyphenyl)nonanoic acid, 640 ml 48% HBr and 640 ml acetic acid was refluxed for 7 hours and cooled to room temperature overnight. The solution was diluted with a large excess of water, whereupon a solid precipitated. The solid was filtered off, re-suspended in water, and filtered again. It was dissolved in ether, washed four times with water, and the organic phase was dried over MgSO₄ overnight. The drying agent was filtered off and the solvent removed in vacuo to give a solid which was recrystallized from toluene to give 31.8 gms (58%) 9(4-hydroxyphenyl)nonanoic acid, m.p. 103°–5°.

Step 2

9(4-Hydroxyphenyl)nonanoic acid, methyl ester

A mixture of 31.8 gms 9(4-hydroxyphenyl)-nonanoic acid, 15 gm molecular sieves (3A), 320 ml methanol, and 5 ml H₂SO₄ was refluxed for 48 hrs. The reaction mixture was cooled, filtered through diatomaceous earth, and the methanol removed in vacuo. The residue was dissolved in CHCl₃, washed twice with 5% NaHCO₃, twice with water, and once with NaCl solution. The aqueous phase was back-washed with ether. The organic layers were filtered, combined, dried over MgSO₄, treated with decolorizing carbon, and filtered through diatomaceous earth. The solvents were removed in vacuo and the resulting solid was crystallized from hexanes:CH₂Cl₂ to give 23.5 gms of product, mp.

52°-4°. A further 4 gms ester was recovered from the mother liquors, after a second crystallization.

Step 3

9(4-Butoxyphenyl)nonanoic acid

A mixture of 7 gms 9(4-hydroxyphenyl)nonanoic acid, methyl ester, 1.45 gms KOH, 100 ml dry dimethoxyethane, and 3.6 gms 1-bromobutane was refluxed with stirring for 24 hrs. The reaction was cooled, filtered through diatomaceous earth, and the solvent was removed in vacuo. The residue was dissolved in $CHCl_3$, washed twice with 5% $Na_2CO_3$, twice with water and once with NaCl solution, and dried over $MgSO_4$. The drying agent was filtered off and the solvent removed in vacuo to give an oil. This oil was stirred overnight at room temperature in a mixture of 70 ml ethanol and 30 ml 10% KOH solution. The solvent was then evaporated in vacuo, the residue dissolved in hot water, cooled, acidified, and the precipitated solid filtered off. The solid was boiled with hexane, filtered, and the solid boiled with cyclohexane and filtered. The insoluble material was again dissolved in water, the aqueous phase acidified with HCl, and the resulting solid was boiled with hexane and filtered. All hexane and cyclohexane solutions were combined and evaporated in vacuo to give 3.5 gms of solid m.p. 45°-8°, which was used directly in the next step.

9(4-Hexyloxyphenyl)nonanoic acid

To a stirring solution of 7 gm 9(4-hydroxyphenyl-nonanoic acid, methyl ester and 1.45 gm KOH in 100 ml dry dimethoxyethane was added 4.3 gms 1-bromohexane. The resulting mixture was refluxed for 24 hrs, cooled, filtered through diatomaceous earth, and evaporated in vacuo. The residue was dissolved in $CHCl_3$, washed twice with 5% $Na_2CO_3$, twice with water and once with NaCl solution, and then dried over $MgSO_4$. The drying agent was filtered off, and the solvent was evaporated in vacuo. The residual oil was stirred overnight with 30 ml 10% KOH and 70 ml ETOH. The solvent was then removed in vacuo, the residue was dissolved in water and acidified to pH 2. The precipitated solid was filtered off and washed with water. This solid was twice boiled with hexane and once with cyclohexane. The combined organic liquids were cooled, filtered, and evaporated in vacuo to give 3.7 gm of product, m.p. 60°-2°, which was used without further purification in the next step.

Step 4

9(4-Hexyloxyphenyl)nonanoyl chloride

A mixture of 3.7 gm 9(4-hexyloxyphenyl)-nonanoic acid and 15 ml thionyl chloride was refluxed for 6 hrs, then concentrated in vacuo to an oil. Since the IR spectrum showed the absence of any acidic H and only a single carbonyl band at 1800 $cm^{-1}$, the oil was used without further purification.

By the same method was also prepared 9(4-butoxyphenyl)nonanoyl chloride.

Step 5

N-Methyl 9(4-Hexyloxyphenyl)nonanohydroxamic acid

To a cold, stirring suspension of 0.6 gm of N-methyl hydroxylamine hydrochloride and 0.7 gms sodium carbonate in 15 ml $CH_2Cl_2$ was added dropwise 2 gms 9(4-hexyloxyphenyl)nonanoyl chloride. The resulting mixture was stirred in the cold for ½ hr, then 0.9 ml water was added and the reaction stirred at room temperature for 22 hr. 100 ml $CH_2Cl_2$ and 40 ml water was added, and the pH of the aqueous layer was adjusted to 3-4 with a few drops of conc. HCl. The organic layers were separated and the aqueous layer was 3×20 ml $CH_2Cl_2$ extracted. The combined organic extracts were washed with water and NaCl solution, and dried over $MgSO_4$. The drying agent was filtered off, the solvent was evaporated in vacuo, and the residue was purified by column chromatography on silica gel in chloroform. The major component had R=0.2. The fractions containing product (as determined by thin layer chromatography) were combined, evaporated in vacuo and the resulting solid recrystallized from hexanes to give 1.0 gm product of m.p. 59°-61°. Elemental analysis calculated C 72.69, H 10.26, N 3.85, O 13.2% found C 72.54, N 10.46, N 3.98%.

Also prepared by this method was:

N-isopropyl 9(4-hexyloxyphenyl)nonanohydroxamic acid, m.p. 79°-81° Elemental analysis: calculated C 73.61, H 10.55, N 3.58, O 12.26% found C 73.63, H 10.65, N 3.74

9(4-Hexyloxyphenyl)nonanohydroxamic acid

To a cold, stirring suspension of 1.2 gms hydroxylamine hydrochloride and 1.7 gms sodium carbonate in 40 ml $CH_2Cl_2$ was added dropwise 4.2 gms 9(4-hexyloxyphenyl)nonanoyl chloride. The mixture was stirred for ½ hr in the cold, then 2 ml water was added, and the reaction was stirred at room temperature overnight. The suspension was then diluted with $CH_2Cl_2$, washed three times with water and once with NaCl solution, then dried over $MgSO_4$. The drying agent was filtered off and the solvent was removed in vacuo to give a solid which was crystallized from $CHCl_3$:hexanes and then hexanes. Impurities were still present by thin layer chromatography, so the solid was dissolved in 3:1 benzene:-hexanes, shaken with 150 gms silica gel, and the silica gel washed with ethyl acetate. The solid remaining on evaporation of the solvent was purified by column chromatography on silica gel with 30% ethyl acetate:$CHCl_3$. The main fraction had Rf=0.4 by thin layer chromatography. The residue from the collected fractions was crystallized twice from $CH_2Cl_2$ to give 0.45 gms product of m.p. 94°-6°.

Elemental analysis: calculated C 72.16, H 10.09, N 4.01% found C 71.83, H 10.34, N 4.00%.

9(4-Butoxyphenyl)nonanohydroxamic acid

To a cold, stirring suspension of 1.1 gm hydroxylamine hydrochloride and 1.5 gms sodium carbonate in 25 ml $CH_2Cl_2$ was added dropwise 3.7 gms 9(4-butoxyphenyl)nonanoyl chloride. This mixture was stirred in the cold for ½ hr and then for 72 hrs at room temperature. The reaction mixture was filtered. The precipitated solid was crystallized three times from $CH_2Cl_2$ (treating with charcoal during the second crystallization) to give 1.1 gms of product of m.p. 99°-101°. Elemental analysis: calculated C 70.99, H 9.72, N 4.36% found C 70.75, H 9.64, N 4.34%.

The enzyme inhibitory activity of these compounds was tested by the same method.

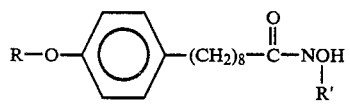

| BMY | R | R' | % Inhibition at 100 μm |
|---|---|---|---|
| 30239 | n-butyl | H | 56.0 |
| 30230 | n-hexyl | H | 0 |
| 30240 | n-hexyl | CH(CH$_3$)$_2$ | 45.8 |
| 30241 | n-hexyl | CH$_3$ | 95.9 |
| 30094 (Comparison) | unsubstituted phenyl | H | 98.3 |

The data shown above indicates that the N-alkylhydroxamic acid derivatives of Formula III are significantly more active than the corresponding hydroxamic acids of Formula II and that the activity of the compounds in the hydroxamic acid series can be significantly increased by alkyl substitution.

We claim:

1. A compound having the formula

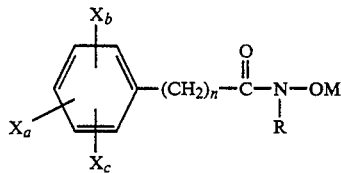   III wherein n is an integer from six to eleven; M is hydrogen or a pharmaceutically acceptable cation; R is (lower)alkyl unsubstituted or substituted by a carboxyl group; and X$_a$, X$_b$ and X$_c$ each independently represent hydrogen (lower)alkyl, (lower)alkenyl, (lower)alkoxy, halo, nitro, hydroxy, amino, cyano, thio, unsubstituted or substituted aryl, unsubstituted or substituted aryl(lower)alkyl, (lower)alkylthio, acyl, acyloxy, acylamino, cycloalkyl having from 3 to 6 carbons, cycloalkyloxy wherein the cycloalkyl groups has from 3 to 6 carbons, (lower)alkylamino and di(lower)alkylamino.

2. A compound according to claim 1 wherein X$_a$, X$_b$ and X$_c$ are independently selected from hydrogen, halo, (lower)alkyl or (lower)alkoxy.

3. A compound according to claim 1 or 2 wherein n is 7, 8 or 9.

4. A compound according to claim 1 or 2 wherein n is 8.

5. A compound according to claim 1 or 2 wherein R is C$_1$-C$_4$ alkyl.

6. A compound having the formula

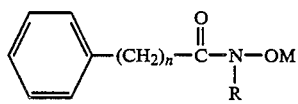

wherein n is an integer from six to eleven; M is hydrogen or a pharmaceutically acceptable cation; and R is C$_1$-C$_4$ alkyl.

7. A compound according to claim 6 wherein n is 6 and R is isopropyl.

8. A compound according to claim 6 wherein n is 7 and R is methyl.

9. A compound according to claim 6 wherein n is 7 and R is isopropyl.

10. A compound according to claim 6 wherein n is 8 and R is methyl.

11. A compound according to claim 6 wherein n is 8 and R is isopropyl.

12. A compound according to claim 6 wherein n is 9 and R is methyl.

13. A compound according to claim 5 wherein n is 9 and R is isopropyl.

14. A compound of the formula

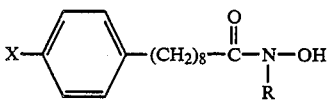

wherein X is C$_1$-C$_6$ alkoxy and R is C$_1$-C$_4$ alkyl.

15. A compound according to claim 14 wherein X is n-hexyloxy and R is methyl.

16. A compound according to claim 14 wherein X is n-hexyloxy and R is isopropyl.

17. A pharmaceutical composition in unit dosage form for the inhibition of 5-lipoxygenase activity in a mammalian host, comprising a 5-lipoxygenase-inhibiting effective amount of a compound of claim 1 and a pharmaceutically acceptable carrier.

18. A method of preventing or treating inflammation in a mammalian host which comprises administering to a host in need of such treatment a therapeutically effective amount of a compound of claim 1.

19. A pharmaceutical composition for preventing or treating inflammation in mammals, which composition comprises a compound of claim 1 in admixture with a pharmaceutically acceptable carrier.

* * * * *